(12) United States Patent
Hopkins et al.

(10) Patent No.: US 6,875,204 B1
(45) Date of Patent: Apr. 5, 2005

(54) UNIVERSAL CONNECTOR

(75) Inventors: Brian J. Hopkins, Mayo (IE); Paul Barron, Sligo (IE); Thomas J. Walsh, Sligo (IE); Bernard Anthony Cotter, Sligo (IE)

(73) Assignee: Abbott Laboratories, Abbott Park, IL (US)

( * ) Notice: Subject to any disclaimer, the term of this patent is extended or adjusted under 35 U.S.C. 154(b) by 124 days.

(21) Appl. No.: 09/608,303

(22) Filed: Jun. 30, 2000

(51) Int. Cl.$^7$ .............................................. A61B 19/00
(52) U.S. Cl. ...................................... 604/414; 604/416
(58) Field of Search ................................ 604/403, 408, 604/411, 414, 416, 249, 93.01, 246–247, 523, 905; 220/287

(56) References Cited

U.S. PATENT DOCUMENTS

| | | | | |
|---|---|---|---|---|
| 1,366,789 A | * | 1/1921 | Graham ...................... | 220/287 |
| 3,019,932 A | | 2/1962 | Singiser | |
| 3,467,270 A | | 9/1969 | Eady | |
| 3,850,341 A | * | 11/1974 | Bart ............................ | 215/228 |
| 4,010,756 A | * | 3/1977 | DuMont et al. ............. | 606/129 |
| 4,614,437 A | * | 9/1986 | Buehler ...................... | 141/319 |
| 4,969,565 A | | 11/1990 | Justal et al. | |
| 5,071,413 A | * | 12/1991 | Utterberg ................... | 604/411 |
| 6,139,564 A | * | 10/2000 | Teoh .......................... | 606/213 |

FOREIGN PATENT DOCUMENTS

| | | |
|---|---|---|
| EP | 0 148 116 A1 | 7/1985 |
| EP | 0 344 070 | 11/1989 |
| EP | 0 355 795 | 2/1990 |
| EP | 0 711 538 | 5/1996 |
| EP | 0 830 874 B1 | 3/1998 |
| EP | 0 930 056 | 7/1999 |
| EP | 0 956 849 A2 | 11/1999 |

OTHER PUBLICATIONS

*Encyclopedia of Polymer Science and Engineering*, vol. 8, John Wiley & Sons, Inc. (New York: 1987), pp. 102–138.
PCT International Search Report.

* cited by examiner

*Primary Examiner*—Angela D. Sykes
*Assistant Examiner*—Leslie Deak
(74) *Attorney, Agent, or Firm*—David L. Weinstein

(57) ABSTRACT

A connector suitable for connection of at least three different types of containers to administration sets, preferably enteral administration sets, and feeding tubes. The containers contain nutritional feed for administration thereof to various types of patients who require enteral nutrition. In one aspect, the connector comprises three different segments:

(a) a first segment for connecting containers having mouths having a relatively large diameter, such as, for example, plastic and glass bottles having mouths having diameters of approximately 40 mm;

(b) a second segment for connecting containers having mouths having a relatively intermediate diameter, such as, for example, crown cap bottles having mouths having diameters of approximately 26 mm; and (c) a third segment for connecting containers having mouths having relatively small diameters, such as, for example, flexible pouches having mouths having diameters of approximately 12.5 mm.

13 Claims, 2 Drawing Sheets

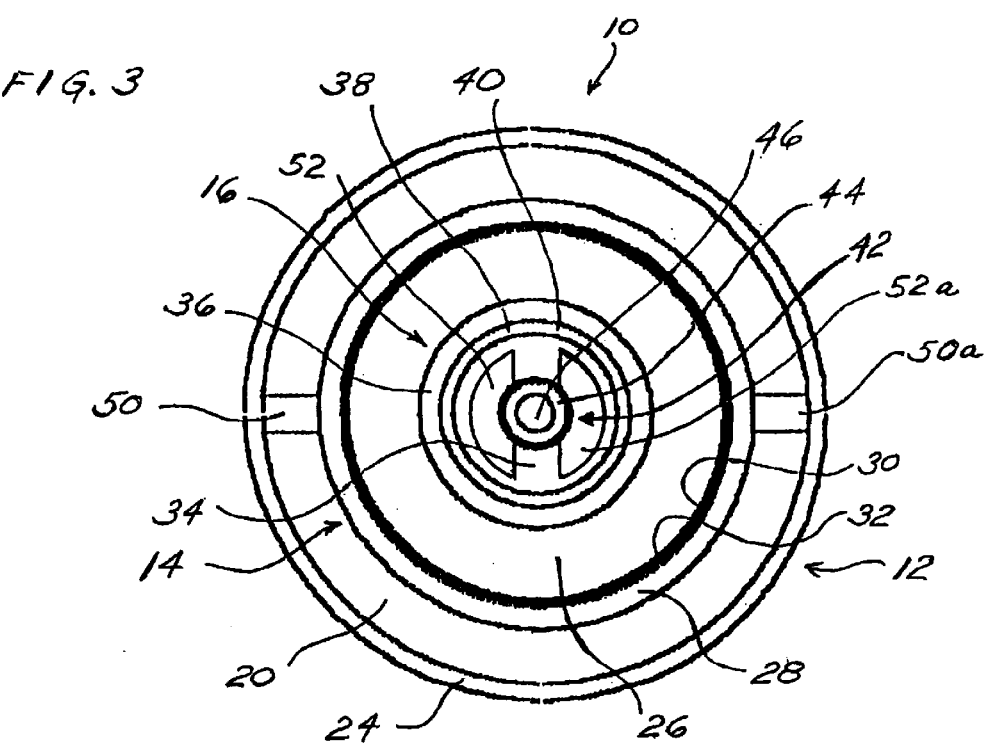

UNIVERSAL CONNECTOR

BACKGROUND OF THE INVENTION

1. Field of the Invention

This invention relates to the field of connectors, and, more particularly, connectors for joining containers to enteral administration sets to provide enteral nutrition.

2. Discussion of the Art

In many areas of patient care, containers of fluids must be connected to enteral administration sets in order to deliver fluids to provide enteral nutrition. There are many types of containers for these fluids. For example, the following types of containers can be used to deliver enteral nutritional feed: glass bottle having 40 mm diameter mouth, plastic bottles having 40 mm diameter mouth, crown cap bottles, and flexible pouches. It is desirable for a given type of connector to be able to be used with more than one type of container.

European Patent No. 0 344 070 B1 discloses a device for connecting an enteral nutrition tube to a nutrient composition container. This device comprises a perforator end piece.

European Patent No. 0 355 795 B1 discloses an adapter for the selective connection of enteral transfer appliances to one each of different bottles whose necks have smaller or greater opening diameters, comprising at least two caps which are disposed coaxially, oriented in the same direction, and have different diameters. One of the caps is rotatable with respect to the other one about a common axis of the caps, while the other cap does not carry out any rotation.

European Patent No. 0 711 538 B1 discloses a universal bottle closure made from thermoplastic material for the random connection of enteral transfer devices to in each case one of numerous bottles, whose necks have a smaller or larger opening diameter. The closure has two caps, which are arranged coaxially with their opening pointing in the same direction and have different opening diameters for forming an annular space, characterized in that the inner cap is made from softer thermoplastic material than the outer cap. The two caps are permanently interconnected and the inner cap has an inwardly projecting sealing flange, constructed for engaging on the sealing face of the smaller diameter bottle, and an outwardly projecting sealing flange, constructed for engagement on the sealing face of the larger diameter bottle.

European patent No. 0 930 056 A2 discloses a universal connector designed for use in various containers having a fluid port for access to the content of the container or for transferring fluid into the container. The universal connector incorporates an elastomeric membrane capable of being ruptured by an access means such as a luer connector or a syringe having a sharp or blunt cannula for fluid communication between the content of the container and the access means.

None of the foregoing connectors is able to connect the major types of containers in use today, such as, for example, (1) glass bottles having a mouth having a diameter of approximately 40 mm, (2) ready-to-hang bottles having a mouth having a diameter of approximately 40 mm, (3) crown cap bottles having a mouth having a diameter of approximately 26 mm, and (4) flexible pouches having a mouth having a diameter of approximately 12.5 mm. Therefore, it would be desirable to provide a connector that can be used to connect all major varieties of feed containers, which containers have mouths having different diameters, to enteral administration sets.

SUMMARY OF THE INVENTION

This invention provides a connector suitable for connection of at least three different types of containers to administration sets, preferably enteral administration sets, and feeding tubes. The containers contain nutritional feed for administration thereof to various types of patients who require enteral nutrition.

In one aspect, the connector comprises three different segments:

(a) a first segment for connecting containers having mouths having relatively large diameters, such as, for example, plastic and glass bottles having mouths having diameters of approximately 40 mm;

(b) a second segment for connecting containers having mouths having relatively intermediate diameters, such as, for example, bottles having crown cap fittings and having mouths having diameters of approximately 26 mm; and (c) a third segment for connecting containers having mouths having relatively small diameters, such as, for example, flexible pouches having mouths having diameters of approximately 12.5 mm.

Each of the three segments comprises a base and a wall projecting from the base. In each segment, the wall surrounds a bore. At one end of each bore is the base. At the other end of each bore is an orifice that communicates directly with the mouth of an appropriate container when the connector is properly joined to the container. The third segment further comprises a spike, projecting from the base of the third segment, for puncturing a seal to obtain access to the contents of a container, such as, for example, a flexible pouch.

Preferably, at least a portion of each of the three segments is cylindrical in shape. The diameter of the orifice of the first segment is greater than the diameter of the orifice of the second segment. The diameter of the orifice of the second segment is greater than the diameter of the orifice of the third segment. The wall of each segment contains means for securely joining the connector to the appropriate container. The exterior wall of the first segment preferably contains at least one thread, more preferably a plurality of threads, in order to provide a screw-fit to the necks of bottles having mouths having relatively large diameters, such as, for example, glass bottles and ready-to-hang bottles. The interior wall of the second segment preferably contains at least one ring in order to provide a snap fit of the second segment of the connector to the necks of bottles having mouths having relatively intermediate diameters, such as, for example, bottles having crown cap fittings. The interior wall of the third segment preferably contains a plurality of threads in order to provide a screw-fit to the necks of containers having mouths having relatively small diameters, such as, for example, flexible feed pouches.

In another aspect, the third segment includes a spike that can be used to break a seal, e.g., a foil seal, of a flexible pouch. This spike, however, can easily be detached from the third segment when the third segment is not to be used for making the appropriate connection, such as, for example, when the connector is to be used with bottles having crown cap fittings. Removal of the spike allows greater flow rates of fluids when the connector is to be used with bottles having crown cap fittings. The spike is typically furnished with a protective sheath to prevent contamination prior to use.

In order to join the connector of this invention to a flexible feed pouch, which is a container that has a mouth having a relatively small diameter, e.g. a diameter of about 12.5 mm, the foil seal of the flexible feed pouch is pierced with the spike, and the third segment is screwed onto the neck of the flexible feed pouch. In order to join the connector of this invention to a bottle having a crown cap fitting, which is a container that has a mouth having a relatively intermediate diameter, e.g., a diameter of about 26 mm, the second segment is snap fit over the neck of the bottle and secured tightly. In order to join the connector of this invention to a glass or plastic bottle, which is a container that has a mouth having a relatively large diameter, e.g., a diameter of about 40 mm, the first segment is screwed onto the threads on the neck of the container.

One advantage of the connector of this invention is the ability to connect at least three major types of containers in use today to a single type of administration set. Another advantage of the connector of this invention is that it can be supplied either alone or it can be supplied as a component of a administration set.

BRIEF DESCRIPTION OF THE DRAWINGS

FIG. 3 is a top plan view of the connector of FIG. 1.

DETAILED DESCRIPTION

Figure 1:
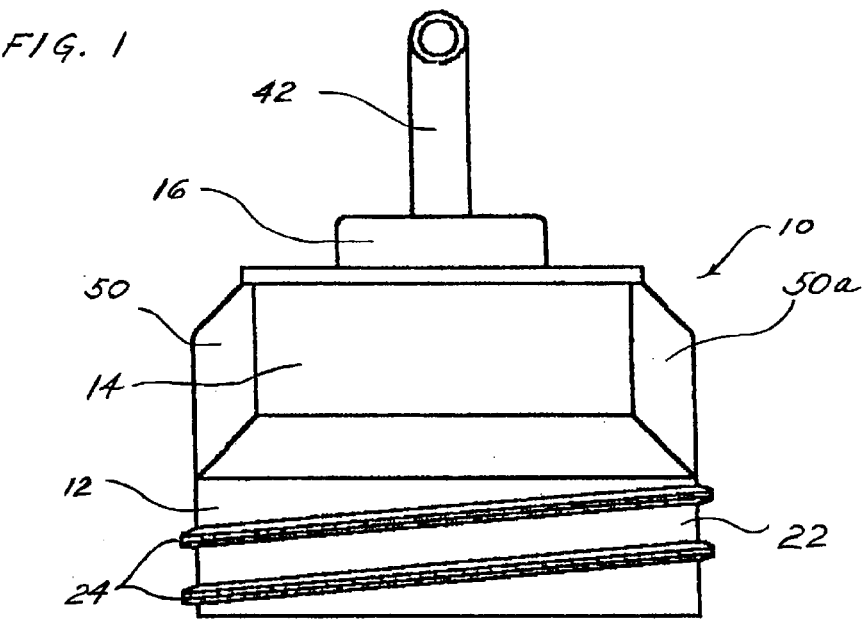
FIG. 1 is a perspective view of one embodiment of the connector of this invention.
Figure 2:
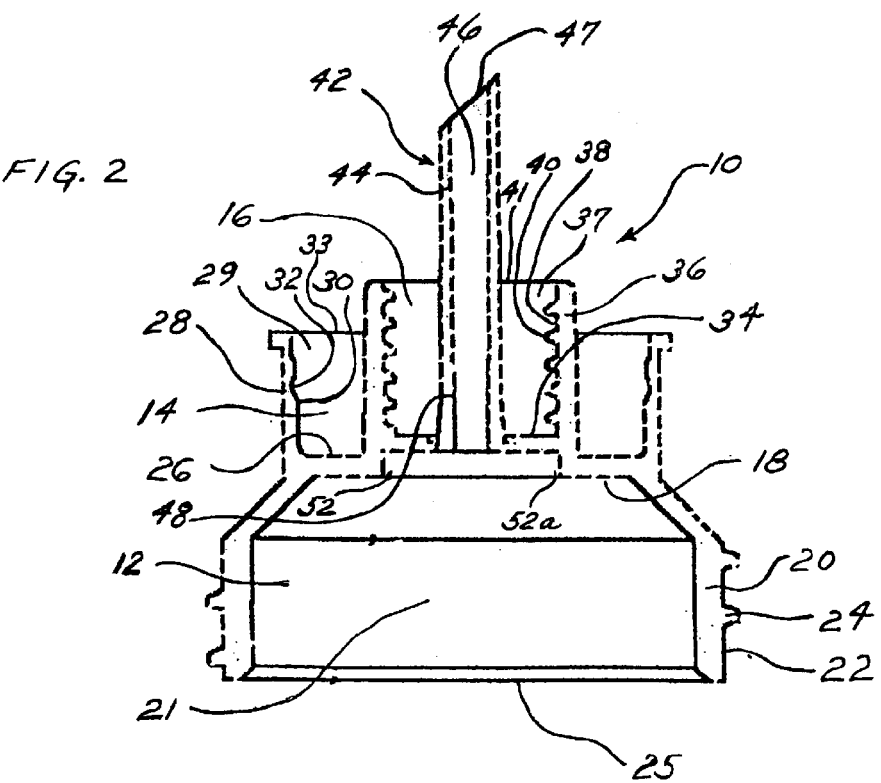
FIG. 2 is a cross-sectional view in elevation of the connector shown in FIG. 1.

Referring now to FIGS. 1, 2, and 3, a connector 10 comprises a first segment 12, a second segment 14, and a third segment 16. The first segment 12 comprises a base 18 having a wall 20 projecting therefrom. The wall 20 surrounds a bore 21. The exterior surface 22 of the wall 20 contains means 24 for attaching the first segment 12 to a container, such as, for example, a bottle, having a mouth having a relatively large diameter, e.g., a diameter of about 40 mm. Means 24 suitable for this invention include, but are not limited to, at least one thread, preferably a plurality of threads. An orifice 25 is located at a position distal from the base 18. This orifice 25 is capable of communicating with the mouth of a container (not shown), such as, for example, a glass bottle or a ready-to-hang bottle, which container has a mouth having a relatively large diameter, e.g., a diameter of approximately 40 mm.

The second segment 14 comprises a base 26 having a wall 28 projecting therefrom. The wall 28 surrounds a bore 29. The interior surface 30 of the wall 28 contains means 32 for attaching the second segment 14 to a container, such as, for example, a bottle, having a mouth having a relatively intermediate diameter, e.g., a diameter of about 26 mm. Means 32 suitable for this invention include, but are not limited to, a ring. An orifice 33 is located at position distal from the base 26. This orifice 33 is capable of communicating with the mouth of a container (not shown), such as, for example, a bottle having a crown cap fitting. This type of container has a mouth having a diameter that is of a size intermediate to that of the diameters of the mouths of containers that can be connected to the first segment 12 and to the third segment 16.

The third segment 16 comprises a base 34 having a wall 36 projecting therefrom. The wall 36 surrounds a bore 37. The interior surface 38 of the wall 36 contains means 40 for attaching the third segment 16 to a container, such as, for example, a flexible pouch, having a mouth having a relatively small diameter, e.g., a diameter of about 12.5 mm. Means 40 suitable for this invention include, but are not limited to, at least one thread, preferably a plurality of threads. An orifice 41 located at a position distal from the base 34 is capable of communicating with the mouth of a container (not shown), such as, for example, a flexible feed pouch, which container has a mouth having a relatively small diameter, e.g., a diameter of approximately 12.5 mm.

The third segment 16 further includes a spike 42 projecting from the base 34. The spike 42 comprises a wall 44 surrounding a bore 46. An orifice 47 located at a position distal from the base 34 communicates with the mouth of a container having a relatively small diameter, such as, for example, a flexible feed pouch. A weakened portion 48 is located at a point close to where the spike 42 joins the base 34 of the third segment 16. This weakened portion 48 allows the user to separate the spike 42 from the connector 10 by breaking the spike 42 away from the connector 10. When the portion of the spike 42 above the weakened portion 48 is thus broken away from the connector 10, the second segment 14 of the connector 10 can be easily used with a container having a mouth having a relatively intermediate diameter, such as, for example, a bottle having a crown cap fitting, the mouth of which bottle typically has a diameter of approximately 26 mm. The weakened portion 48 can be provided by means of perforations, a slit, a notch, or by making the weakened portion thinner than the remainder of the spike. One of ordinary skill in the art would have the ability to provide such a weakened portion 48 to the spike 42. The end of the spike 42 distal from the base 34 is beveled in order to provide that end with a sharp edge to facilitate puncturing the seal of a container, such as, for example, a foil seal on a flexible feed pouch.

As shown in FIGS. 1, 2, and 3, the first segment 12 is not cylindrical along its entire length. The wall 20 of the first segment 12 tapers at approximately a 45° angle to span the distance between the base 18 and the portion of the wall 20 that is perpendicular to the base 18. This tapered section is not required; the first segment 12 could have been cylindrical along its entire length. As shown in FIGS. 1 and 3, a tab 50 and a tab 50a are located on the exterior surface of the second segment 14. The tab 50 is preferably set off about 180° from tab 50a. The tab 50 and the tab 50a can be gripped by the user to facilitate tightening of the connector 10 to a container, particularly when the connection is made by screwing the connector 10 onto the neck of a container. The connector 10 preferably contains residue outlets 52 and 52a, in order to allow liquid residue accumulating in the well of the third segment 16 to flow more rapidly when the second segment 14 is attached to a container having a mouth having a diameter of relatively intermediate size.

The dimensions of each segment are not critical, but the following dimensions are provided to give an indication of the size of a typical connector of this invention. The thickness of the wall 20 preferably is about 0.06 inch. The thickness of the wall 28 is preferably about 0.06 inch. The thickness of the wall 36 is preferably about 0.06 inch. The inside diameter of the first segment 12 is preferably about 1.37 inches. The inside diameter of the second segment 14 is preferably about 1.00 inch. The inside diameter of the third segment 16 is preferably about 0.50 inch. The outside diameter of the first segment 12 is preferably about 1.49 inches. The outside diameter of the second segment 14 is preferably about 1.12 inches. The outside diameter of the third segment 16 is preferably about 0.62 inch.

The frequency of the threads on the threaded segments is not critical, but it is preferred that there be about six threads per inch. The specific number of threads on the threaded segments is not critical, but it is preferred that the first segment 12 contain two threads and that the third segment 16 contain five threads. The length of the first segment 12 is preferably sufficient to contain two threads. The length of the second segment 14 is preferably sufficient to contain a ring for a snap fit. The length of the third segment 16 is preferably sufficient to contain five threads. However, the length of each of the three segments is not critical. The length of the spike is preferably sufficient to pierce the foil of a flexible feed pouch and protrude into the pouch. A typical length of the spike is about 1.25 inches. A typical length of the connector is about 1.85 inches, measured from the tip of the spike to the orifice 25 of the first segment 12. A typical length of the first segment 12 is about 0.58 inch. A typical length of the second segment is about 0.5 inch. A typical length of the third segment (not including the spike) is about 0.5 inch.

Types of containers that can be joined to the first segment 12 include plastic and glass bottles, typically having a mouth of relatively large diameter, such as, for example, a diameter of approximately 40 mm. Types of containers that can be joined to the second segment 14 include bottles having crown cap fittings, flexible pouches, and bottles made of glass or plastic. These containers have diameters of relatively intermediate size, such as, for example, a diameter of approximately 26 mm. Types of containers that can be joined to the third segment 16 include flexible containers having a mouth having a relatively small diameter, such as, for example, a diameter of approximately 12.5 mm.

The connector of this invention is preferably made by means of injection molding. Processes of injection molding are described in, for example, *Encyclopedia of Polymer Science and Engineering*, Volume 8, John Wiley & Sons, Inc. (New York: 1987), pp. 102–138, incorporated herein by reference. Materials suitable for making the connector of this invention include moldable polymeric materials, such as, for example, polyethylene, e.g., high density polyethylene.

The connector of this invention is versatile and can be used with numerous types of containers. In the case of a container having a crown cap fitting, the second segment 14 of the connector 10 is snap-fit onto the neck of the bottle. In the case of a plastic or glass bottle having a mouth having a diameter of about 40 mm, the first segment 12 is joined to the neck of the bottle by means of the threads 24. In the case of a flexible pouch, the spike 42 is used to puncture the foil seal covering the mouth of the pouch, and then the third segment 16 is joined to the neck of the pouch by means of the threads 40. When the first segment 12 or the second segment 14 is used, the spike 42 is unnecessary. When the spike 42 is unnecessary, the weakened portion 48 allows the user to break off the tip of the spike 42 and discard it.

The advantages of the connector of the present invention include the following:

(1) the connector can be used with at least three different types of containers—(a) containers, such as, for example, flexible pouches, which containers have mouths having relatively small diameters; (b) containers, such as, for example, bottles having crown cap fittings, which containers have mouths having relatively intermediate diameters; and (c), and containers, such as, for example, ready-to-hang bottles and glass bottles, which containers have mouths having relatively large diameters;

(2) the spike can be disposed of when not necessary;

(3) the connector of this invention has the ability to connect at least three major types of containers in use today to a single type of administration set; and (4) the connector of this invention can be supplied either alone or it can be supplied as a component of a administration set.

Various modifications and alterations of this invention will become apparent to those skilled in the art without departing from the scope and spirit of this invention, and it should be understood that this invention is not to be unduly limited to the illustrative embodiments set forth herein. For example, the threads on a segment containing threads can be replaced by a ring if it is desired to modify that thread-containing segment so that it can be used with a container having a neck having a crown cap fitting. Also, the ring on the segment containing a ring for use with a crown cap fitting can be replaced by one or more threads if it is desired to modify that ring-containing segment so that it can be used with a container having a neck having threads. Also, the dimensions set forth herein are merely approximate. Those skilled in the art can vary these dimensions to render the connector of this invention suitable for different types of containers.

What is claimed is:

1. A connector suitable for use with a plurality of containers, said connector comprising:

a first segment capable of connecting a container having a mouth having a relatively large diameter;

a second segment capable of connecting a container having a mouth having a relatively intermediate diameter; and a third segment capable of connecting a container having a mouth having a relatively small diameter, wherein said third segment has a base having a wall projecting from said base to form a well, said base of said third segment having at least one opening, wherein said opening is configured to allow residual liquid accumulating in said well of said third segment to flow into said second segment, whereby when said second segment is attached to a container having a mouth having a diameter of relatively intermediate size, said residual liquid accumulating in said well of said third segment flows more rapidly.

2. The connector of claim 1, wherein at least a portion of each of said first segment, said second segment, and said third segment is cylindrical in shape.

3. The connector of claim 1, wherein each of said first segment, said second segment, and said third segment has an orifice that is substantially circular in shape.

4. The connector of claim 3, wherein the diameter of said orifice of said first segment is greater than the diameter of said orifice of said second segment.

5. The connector of claim 3, wherein the diameter of said orifice of said second segment is greater than the diameter of said orifice of said third segment.

6. The connector of claim 1, wherein said first segment has means thereon for joining said connector to the neck of a container.

7. The connector of claim 6, wherein said means for joining said connector to the neck of a container comprises at least one thread.

8. The connector of claim 1, wherein said second segment has means thereon for joining said connector to the neck of a container.

9. The connector of claim 8, wherein said means for joining said connector to the neck of a container comprises a ring.

10. The connector of claim 1, wherein said third segment has means thereon for joining said connector to a container.

11. The connector of claim 10, wherein said means for joining said connector to the neck of a container comprises at least one thread.

12. The connector of claim 1, wherein said third segment has a spike projecting from said base.

13. The connector of claim 12, wherein said spike includes a weakened portion, whereby said spike can be removed from said connector.

* * * * *